United States Patent [19]

Osborne

[11] Patent Number: 5,631,301
[45] Date of Patent: May 20, 1997

[54] TOPICAL ANTIBIOTIC COMPOSITION PROVIDING OPTIMAL MOISTURE ENVIRONMENT

[75] Inventor: David W. Osborne, The Woodlands, Tex.

[73] Assignee: ViroTex Corporation, The Woodlands, Tex.

[21] Appl. No.: 313,417

[22] Filed: Sep. 27, 1994

[51] Int. Cl.[6] .................................................. A61K 9/107
[52] U.S. Cl. ........................ 514/772.4; 424/405; 424/409
[58] Field of Search ............................... 424/486, 445, 424/443, 78.07, 78.06, 78.02, 405, 409; 514/772.4

[56] References Cited

U.S. PATENT DOCUMENTS

| | | | |
|---|---|---|---|
| 3,328,259 | 6/1967 | Anderson | 167/84 |
| 3,579,465 | 5/1971 | Schmolka | 252/316 |
| 4,007,263 | 2/1977 | Pichierri | 424/78 |
| 4,226,232 | 10/1980 | Spence | 128/156 |
| 4,300,555 | 11/1981 | Kopito | 128/248 |
| 4,307,717 | 12/1981 | Hymes et al. | 128/156 |
| 4,326,977 | 4/1982 | Schmolka | 252/106 |
| 4,393,048 | 7/1983 | Mason, Jr. et al. | 424/132 |
| 4,430,325 | 2/1984 | Gaffar et al. | 424/601 |
| 4,474,753 | 10/1984 | Haslam et al. | 424/78 |
| 4,552,138 | 11/1985 | Hofeditz et al. | 128/156 |
| 4,554,317 | 11/1985 | Behar et al. | 525/28 |
| 4,646,730 | 3/1987 | Schonfeld et al. | 728/156 |
| 4,664,906 | 5/1987 | Sipos | 424/49 |
| 4,678,664 | 7/1987 | Schmolka | 424/65 |
| 4,728,323 | 3/1988 | Matson | 604/304 |
| 4,842,597 | 6/1989 | Brook | 604/368 |
| 4,880,416 | 11/1989 | Horiuchi et al. | 604/307 |
| 4,889,530 | 12/1989 | Smith et al. | 604/304 |
| 4,954,338 | 9/1990 | Mattox | 424/78 |
| 4,997,867 | 3/1991 | Jederstrom et al. | 524/47 |
| 5,061,689 | 10/1991 | Alvarez | 514/6 |
| 5,126,141 | 6/1992 | Henry | 424/423 |
| 5,147,338 | 9/1992 | Lang et al. | 604/304 |
| 5,147,339 | 9/1992 | Sundstrom | 604/307 |
| 5,156,601 | 10/1992 | Lorenz et al. | 604/307 |
| 5,204,110 | 4/1993 | Cartmell et al. | 424/443 |
| 5,206,026 | 4/1993 | Sharik | 424/445 |
| 5,275,805 | 1/1994 | Nabi, et al. | 424/54 |
| 5,322,689 | 6/1994 | Hughes et al. | 424/401 |
| 5,336,501 | 8/1994 | Czech et al. | 424/445 |

OTHER PUBLICATIONS

PCT Search Report for PCT/US95/12276.
Dialog Patent and Literature Search Report, 1994.

*Primary Examiner*—Thurman K. Page
*Assistant Examiner*—M. Sikha
*Attorney, Agent, or Firm*—Arnold, White & Durkee

[57] ABSTRACT

A composition for the treatement of wounds comprising a topical semisolid composition capable of providing a prophylaxis against infection, wherein the semisolid composition maintains constant moisture by promoting increased water content in wounds becoming dry and reduced water content in wounds having excess exudate. The topical semisolid composition is used in conjunction with antibiotic formulations.

2 Claims, No Drawings

TOPICAL ANTIBIOTIC COMPOSITION PROVIDING OPTIMAL MOISTURE ENVIRONMENT

BACKGROUND OF THE INVENTION

1. Field of the Invention

This present invention relates to antibiotic carriers which exhibit optimal water absorption/retention properties for the promotion of wound healing.

2. Background of the Invention

While minor cuts, burns and abrasions seldom become infected, any break in the skin can lead to localized or even systemic infection. This is of special concern in children who may not have fully developed immune systems, or in immunocompromised individuals.

Recently, it has been shown that the amount of moisture retained in equilibrium with wounded skin, i.e. cuts, burns and abrasions, dramatically alters the healing of the wound. While an uncovered wound or loosely covered wound—exemplified by a minor cut or abrasion covered only by a flexible fabric bandage—will quickly form a hard crust or scab, this represents the least favorable environment for quick healing with minimal scarring. The only advantage of hard crust formation is that the wound tissue is thoroughly sealed from contamination by pathogens from the environment or adjacent intact skin. The disadvantage of the body's naturally evolved healing process is that fibroblasts, macrophages and other cellular repair mediators can only slowly migrate to, and function in, the wound area that is covered by dry crust. Limited mobility of fibroblast results in abnormal collagen production in the dermis which results in scarring. It is important to understand that the human body's only mechanism of infection prophylaxis, namely scabbing, results in extended time to healing of the wound and increased dermal scarring upon completion of the healing process.

The ideal environment for wound healing is a moist environment. Ideally, the moist environment should provide sufficient fluid such that the mobility of tissue repair mediators is not limited, but not so much fluid that these mediators are expelled from the tissue being repaired. As described above for an uncovered or loosely covered cut or minor abrasion, the scab results in a dry wound environment that does not have sufficient fluid to allow optimal mobilization of tissue repair mediators. Conversely, more extensive abrasions and burns, particularly after an initial hypoprofusion state, can be highly exuding wounds that are "too wet," resulting in expulsion of tissue repair mediators. Optimal therapy of these wounds requires that a significant amount of the water be removed from the wound while the tissue repair mediators remain mobile and in contact with the wounded tissue. Thus, for optimal healing, i.e., rapid healing with minimal scarring, a controlled moist environment must be maintained such that moisture is allowed to permeate a wound which becomes too dry (i.e., dry crust or scab forming) and also allowed to escape from a wound which becomes too wet (i.e., heavily exudating).

While this moisture balance for a wound can be accomplished using semipermeable wound dressings, such coverings may actually hinder the healing process when placed in direct contact with the wound site. In particular, the wounded skin or repair mediators may attach to the bandage matrix resulting in introduction of a new wound upon dressing removal, or at least immobilization or removal of repair mediators. Also, semi-permeable wound dressings provide no prophylaxis against infection. As a consequence, the wound is highly prone to microbial colonization and possible infection during the healing process. Finally, wound dressings tend to be expensive, not only in terms of the cost of materials, but also in terms of the nursing time required for dressing changes.

In consideration of cost, ease of use, prophylaxis of infection, and provision of an optimal wound healing environment, the preferred treatment of wounds would be a topical semisolid containing antimicrobial actives having a broad defense against infection and being capable of maintaining a moist wound environment by promoting increased water content in wounds becoming dry and promoting reduction of water content in wounds becoming too wet. In the past, triple antibiotic topicals prepared in hydrophobic ointment vehicles have been used to provide prophylaxis against infection and promote increased water retention in wounds due to the occlusive nature of the hydrophobic ointment system. However, these products cannot promote reduction of water content in wounds which are highly exudating, because the ointment floats to the top of the exudate and is removed from the wound site. Thus, triple antibiotic topicals formulated in hydrophobic ointments are inappropriate for use on highly exudating wounds (i.e., burns and deep abrasions) because the product is quickly removed from the wound site making it ineffective both for infection prophylaxis and optimal wound healing.

Better carriers are needed for the triple antibiotic agents.

SUMMARY OF THE INVENTION

The present invention comprises a composition for the treatment of wounds. The composition comprises a topical semisolid composition capable of providing prophylaxis against infection, wherein said composition maintains a moist environment for a wound upon application by promoting increased water content in wounds becoming dry and promoting reduced water content in wounds having excess exudate, and an antibiotic formulation.

In one embodiment of the present invention, the antibiotic formulation comprises one or more of the antibiotics "listed in 21 C.F.R. §444," (1995), which include amikacin, amilkacin sulfate, dihydrostreptomycin sulfate, crystalline dihydrostreptomycin sulfate, dihydrostreptomycin hydrochloride, gentamicin sulfate, sterile gentamicin sulfate, kanamycin sulfate, sterile kanamycin sulfate, neomycin sulfate, sterile neomycin sulfate, netilmicin sulfate, paramomycin sulfate, sisomicin sulfate, sterile streptomycin sulfate, tobramycin and sterile tobramycin sulfate. In another embodiment the topical semisolid comprises a blend of polyethylene glycols. In still another embodiment the topical semisolid comprises a hydrophilic gel or hydroalcoholic gel having a gelling agent.

DESCRIPTION OF THE PREFERRED EMBODIMENTS

The present invention is directed to novel, antibiotic carrier compositions which exhibit optimal water absorption/retention properties for the promotion of wound healing with minimal scarring upon combination with antibiotic agents. The compositions of the present invention comprise topical semisolid carrier agents which are suitable for use in all types of wounds, particularly wounds associated with minor cuts, abrasions, and burns. The advantages of the present invention are appreciated in antibiotic applications to wound sites for prevention of infection and promotion of optimal wound healing, and are particularly effective when the semisolid carrier agents are used in combination with triple antibiotic formulations known to those skilled in the art.

The carrier compositions of the present invention comprise gel-like vehicles which are capable of incorporating water to at least 30% of their initial application weight, and when left at ambient conditions on a non-absorbing surface, retain at least 60% of their application weight for two hours. Topical preparations having these water absorption/retention properties have been proven to provide an optimal moisture environment for rapid wound healing with minimal scarring. Examples of vehicles which exhibit these water absorption/retention properties include polyethylene glycols as well as hydrophilic and hydroalcoholic compounds.

The glycol compositions of the present invention typically exhibit semisolid properties in pure form, permitting direct application of the glycol compositions to wound sites without the addition of gelling agents. On the other hand, gelling agents may be added to the hydrophilic and hydroalcoholic compounds to provide an optimal semisolid composition for wound applications.

Some preferred gelling agents for use with the hydrophilic or hydroalcoholic compounds include hydroxyethylcellulose (commercially available as Natrosol® hydroxyethylcellulose produced by Aqualon), cross-linked acrylic acid polymers (such as the commercially available product "CARBOPOL®" cross linked acrylic acid polymer, produced by Goodrich), PVM/MA decadiene crosspolymer copolymer (such as the commercially available product "STABILEZE®" PVM/MA decadiene crosspolymer, produced by ISP), ammonium acrylates/acrylonitrogens (commercially available as "HYPAN®" ammonium acrylates/acrylonitrogens) and the like. It is preferred that the gelling agent comprise between about 0.5% to about 6% by weight of the composition. More particularly, for "CARBOPOL®" cross linked acrylic acid polymer the preferred compositional weight percent range is between about 2% to about 6%, while for "NATROSOL®" hydroxyethylcellulose the preferred range is between about 0.5% to about 4%. Furthermore, the preferred compositional weight percent range for "STABILEZE®" PVM/MA decadiene crosspolymer and "HYPAN®" ammonium acrylates/acrylonitrogens is between about 1% to about 4%.

Typical antibiotic formulations useful in the present invention include: Silver Sulfadiazine, preferably comprising about 0.2% to about 5% by weight of the total antibiotic carrier composition; Neomycin, preferably about 0.1% to 2% by weight of the composition; Gramicidin, preferably 0.01% to 0.1% by weight; Chlortetracycline hydrochloride, preferably 1% to 5% by weight; Medocycline sulfosalicylate, preferably 0.2% to 4% by weight; Oxytetracycline, preferably 1% to 5% by weight; Tetracycline hydrochloride, preferably 0.05% to 5% by weight; about 2000 to 10,000 units of Polymyxin B; or about 200 to 1000 units of Bacitracin. The above antibiotic formulations are for illustration only, and do not represent an exhaustive list of the antibiotics that may be utilized. Those of skill in the art will recognize other antibiotic formulations that may be utilized and the typical amounts that would be useful in the present invention.

To determine the degree of water absorption achieved by the carrier compositions of the present invention, approximately two grams of the vehicle was exactly weighed into a 15 ml vial. Water equivalent to 30% by weight of the vehicle (weight of vehicle×0.3=wt of water added) was subsequently added to the vial and thoroughly mixed. The vehicle was then visually examined for indications of the extent of water incorporation. If all of the water was incorporated immediately after mixing, then the formulation was determined to be capable of incorporating moisture to at least 30% of its initial application weight.

The method of determining water retention of the compositions of the present invention was conducted by applying the water-laden carrier samples to the surface of a tared watch glass to a thickness of approximately 1–2 mm. The weight of the vehicle was then accurately determined and the vehicle-coated watch glass exposed to ambient laboratory conditions. The weight of the tared watch glass containing the vehicle was then accurately weighed after two hours, and the percent application weight after the two hour ambient exposure time was calculated according to the following formula:

$$[\{(\text{final weight of vehicle}+\text{tare weight watch glass})-\text{tared weight watch glass}\}\div\{(\text{initial weight of vehicle}+\text{tare weight watch glass})-\text{tared weight of watch glass}\}].$$

The following examples detail the results of the experimental tests and are provided to illustrate the water absorption/retention abilities of the compositions of the present invention. However, these examples are not intended, nor should they be construed, to limit the scope of the present invention.

EXAMPLE 1

30 wt % Polyethylene Glycol (PEG) 3350 and 70 wt % Polyethylene Glycol (PEG) 400 incorporated at least 30% water and retained 100% of its application weight.

EXAMPLE 2

20 wt % PEG 3350 and 80% PEG 400 incorporated at least 30% water and retained 100% of its application weight.

EXAMPLE 3

40 wt % PEG 3350 and 60% PEG 400 incorporated at 30% water and retained 100% of its application weight.

EXAMPLE 4

50 wt % PEG 3350 and 50% PEG 400 incorporated at least 30% water and retained 100% of its application weight.

EXAMPLE 5

2% "CARBOPOL 980®" cross linked acrylic acid polymer in water incorporated at least 30% water and retained 61% of its application weight.

EXAMPLE 6

4% "CARBOPOL 980®" cross linked acrylic acid polymer in water incorporated at least 30% water and retained 70% of its application weight.

EXAMPLE 7

6% "CARBOPOL 980®" cross linked acrylic acid polymer in water incorporated at least 30% water and retained 67% of its application weight.

EXAMPLE 8

1% "HYPAN®" ammonium acrylates/acrylonitrogens in water incorporated at least 30% water and retained 62% of its application weight.

EXAMPLE 9

4% "HYPAN®" ammonium acrylates/acrylonitrogens in water incorporated at least 30% water and retained 67% of its application weight.

EXAMPLE 10

0.5% "NATROSOL®" hydroxyethylcellulose in water incorporated at least 30% water and retained 64% of its application weight.

EXAMPLE 11

1% "NATROSOL®" hydroxylethycellulose in water incorporated at least 30% water and retained 64% of its application weight.

EXAMPLE 12

2% "NATROSOL®" hydroxylethycellulose in water incorporated at least 30% water and retained 64% of its application weight.

EXAMPLE 13

4% "NATROSOL®" hydroxylethycellulose in water incorporated at least 30% water and retained 61% of its application weight.

EXAMPLE 14

1% "STABILEZE®" PVM/MA decadiene crosspolymer in water incorporated at least 30% water and retained 60% of its application weight.

EXAMPLE 15

2% "STABILEZE®" PVM/MA decadiene crosspolymer in water incorporated at least 30% water and retained 60% of its application weight.

EXAMPLE 16

4% –STABILEZE®" PVM/MA decadiene crosspolymer in water incorporated at least 30% water and retained 65% of its application weight.

Those skilled in the art will recognize that, while specific embodiments have been illustrated and described, various modifications and changes may be made without departing from the spirit and scope of the invention.

What is claimed:

1. A composition for the treatment of wounds comprising:
    a topical semisolid composition which is capable of providing a moist environment for a wound by promoting increased water content in wounds becoming dry and promoting reduced water content in wounds having excess exudate, comprising vehicles, which are capable of incorporating water to at least 30% of their initial application weight, while also being capable of retaining at least 60% of their application weight for two hours when left at ambient conditions on a non-absorbing surface;
    and an antibiotic formulation, wherein the topical semisolid comprises a hydrophilic gel or hydroalcoholic gel having between about 1% to about 4% ammonium acrylates/acrylonitrogen copolymer as the gelling agent.

2. A composition for the treatment of wounds comprising:
    a topical semisolid composition which is capable of providing a moist environment for a wound by promoting increased water content in wounds becoming dry and promoting reduced water content in wounds having excess exudate, comprising vehicles, which are capable of incorporating water to at least 30% of their initial application weight, while also being capable of retaining at least 60% of their application weight for two hours when left at ambient conditions on a non-absorbing surface;
    and an antibiotic formulation, wherein the topical semisolid comprises a hydrophilic gel or hydroalcoholic gel having between about 1% to about 4% PVM/MA decadiene crosspolymer as the gelling agent.

* * * * *